(12) United States Patent
Garito et al.

(10) Patent No.: US 6,458,124 B1
(45) Date of Patent: Oct. 1, 2002

(54) ELECTROSURGICAL HANDLE FOR BIPOLAR/UNIPOLAR ELECTRODES

(76) Inventors: Jon C. Garito, 1135 Railroad Ave., Hewlett, NY (US) 11557; Alan G. Ellman, 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/821,364

(22) Filed: Mar. 30, 2001

Related U.S. Application Data

(60) Division of application No. 09/413,171, filed on Oct. 7, 1999, now Pat. No. 6,238,394, which is a continuation-in-part of application No. 09/393,286, filed on Sep. 10, 1999, now Pat. No. 6,210,409, and a continuation-in-part of application No. 09/303,839, filed on May 3, 1999, now Pat. No. 6,231,571.

(51) Int. Cl.[7] ............................................... A61B 18/18
(52) U.S. Cl. ............................. 606/41; 606/45; 606/49; 606/50
(58) Field of Search ............................. 606/32, 34, 37, 606/39, 40, 41, 45, 46, 47, 48, 49, 50; 604/20, 22

(56) References Cited

U.S. PATENT DOCUMENTS

| 4,711,239 A | * | 12/1987 | Sorochenko et al. | ........ 219/234 |
| 5,186,714 A | * | 2/1993 | Boudreault et al. | ........... 604/21 |
| 5,256,138 A | * | 10/1993 | Burek et al. | .................. 606/42 |

* cited by examiner

*Primary Examiner*—Rosiland S. Kearney

(57) ABSTRACT

An electrosurgical instrument having a universal handle that is adopted for mounting and unmounting of different core assemblies for carrying out various electrosurgical procedures. The mounting and unmounting is accomplished by constructing the handle in several parts with upper concave portions configured to receive and hold the core assemblies which are provided with similar outer housings so they all can fit within the concave portions. The handle parts are held together with detent mechanisms which allow them to be easily snapped together and apart as desired. The handle can accommodate a variety of core assemblies that can comprise parts of a family of assemblies capable of both unipolar and bipolar electrosurgical procedures, and thus provides a very flexible instrument for the active surgeon.

14 Claims, 5 Drawing Sheets

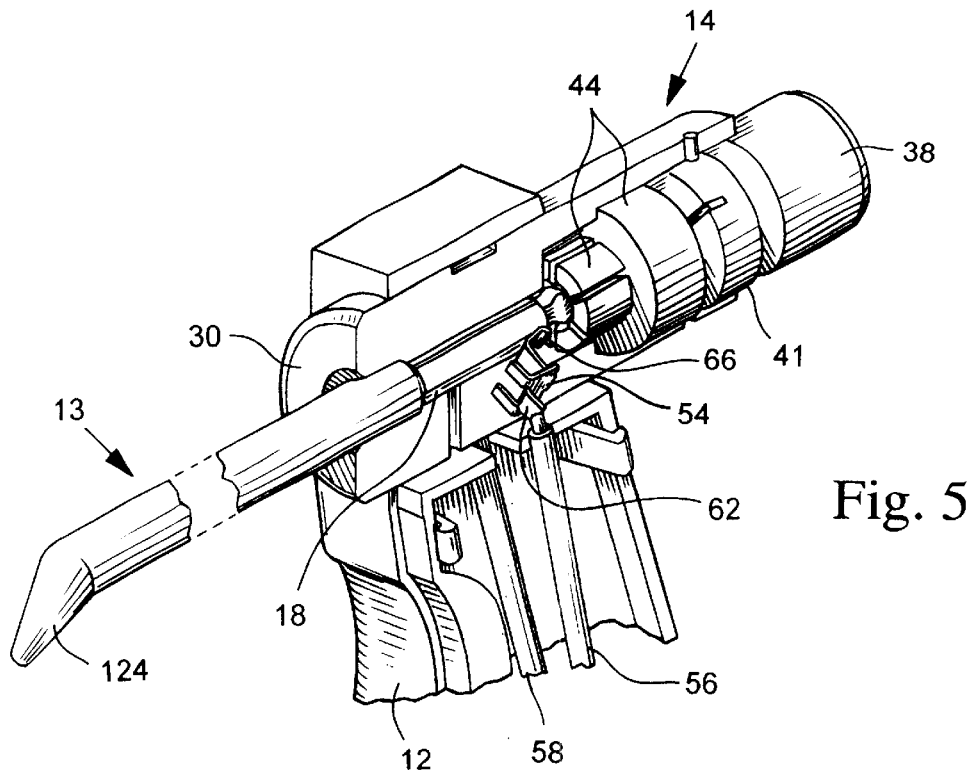
Fig. 5
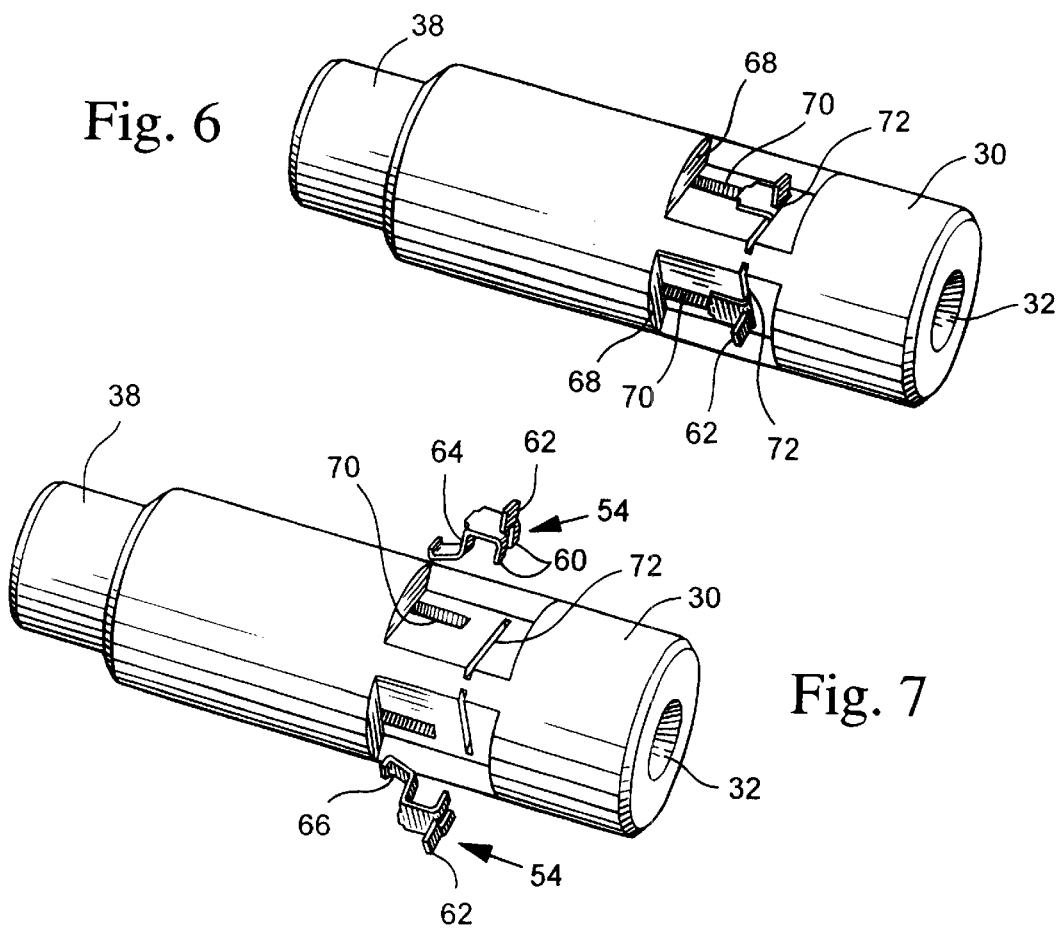
Fig. 6
Fig. 7

ELECTROSURGICAL HANDLE FOR BIPOLAR/UNIPOLAR ELECTRODES

RELATED APPLICATIONS

This application is a division of application Ser. No. 09/413,171, filed Oct. 7, 1999, now U.S. Pat. No. 6,238,394.

U.S. application Ser. No. 09/303,839, filed May 3, 1999, U.S. Pat. No. 6,231,571 commonly owned, for "Electrosurgical Handpiece For Treating Tissue", of which the present application is a continuation-in-part.

U.S. application Ser. No. 09/393,286, filed Sep. 10, 1999, U.S. Pat. No. 6,210,409 commonly owned, for "Electrosurgical Handpiece For Treating Tissue", of which the present application is a continuation-in-part.

This invention relates to electrosurgical handles for interchangeably supporting bipolar or unipolar electrodes for use in an electrosurgical procedure.

BACKGROUND OF THE INVENTION

Our prior application, Ser. No. 09/303,839, describes a novel electrosurgical handpiece for treating tissue in a surgical procedure commonly known as minimally invasive surgery (MIS). Among the features described and claimed in the prior application is an electrosurgical handpiece that can be used in MIS and allows a surgeon or other practitioner to replace in the handle a bipolar electrode with a unipolar electrode, or vice-versa, in the midst of a surgical procedure. For example, the surgeon may desire to use a particular unipolar electrode for a cutting procedure and follow it up using a bipolar electrode to coagulate any bleeders. This is achieved in one embodiment by a handle construction to accommodate other electrode ends, by sliding out an inner tubular member from an outer tubular member and sliding in its place another inner tubular member with a different electrode configuration. This can be done before the outer tubular member is extended through a cannula into the patient or even while the cannula is in place within the patient. In addition, a bipolar assembly in its dual lumen arrangement can be replaced by a unipolar electrode in a lumen with only a single compartment, in which case, the unipolar electrode end, with one of the several electrode shapes, would project forward from the end of the inner tubular member. When an electrode substitution is to be made, the surgeon can pull out the inner tubular member and replace it with another inner tubular member with a different electrode thereby enabling the surgeon to change electrodes during the procedure without removing the handle with its outer tubular member that has already been strategically placed in the surgical site, That concept of interchangeable unipolar and bipolar electrodes has been extended in the present application to cover the use of many conventional as well as novel electrode constructions.

SUMMARY OF THE INVENTION

The present invention is a continuation-in-part of both prior application, Ser. Nos. 09/303,839 and 09/393,286, and hereby incorporates by reference the total contents of both prior applications. The present invention describes a novel handle construction that allows different what will be referred to herein as electrode core assemblies to be mounted in a universal handle for independent use as needed. The cores in preferred embodiments comprise a bipolar core, a unipolar core, and a turbinate core, but it will be understood that the invention is not limited to just those three cores but contemplates the use of other cores configured to be mounted in the common handle.

In a preferred embodiment, the universal handle is constructed in multiple detachable parts held together by, preferably, a detent construction that uses locking projections on one handle part that detachably snap into corresponding slots on the other handle part. The parts are detached to remove one core assembly and replace it with another core assembly.

In another preferred embodiment, the replaceable unipolar core comprises a collet subassembly that can be operated by the practitioner to hold any one of a number of standard unipolar electrodes.

In another preferred embodiment, the replaceable bipolar core comprises a electrode subassembly that can be operated by the practitioner to hold any one of a number of different bipolar electrodes.

In still another preferred embodiment, the replaceable turbinate core comprises a socket subassembly that can be operated by the practitioner to hold any one of a number of turbinate electrodes.

The present description will be confined mainly to the construction of the handle and core assemblies which when mounted in the handle are capable of accommodating many well-known and commercially available unipolar electrodes as well as bipolar electrodes of the type described in the copending referenced applications.

The present invention also makes use of the interchangeability of electrodes. As explained in connection with FIG. 1 of the earlier filed prior application, the various bipolar electrodes can be withdrawn from the handpiece and replaced by another bipolar or unipolar electrode enabling the surgeon to successively use one or more bipolar or unipolar electrodes as needed. So, for example, after first using a bipolar or unipolar electrode for a cutting procedure, either of the electrodes of the present invention can be substituted to perform hemostasis of any blood vessels cut during the procedure.

The construction of the invention will provide the same important benefits not only for MIS of herniated disks but also for other MIS procedures where controlled electrode position and controlled heat generation is of importance as described in the prior application. It will also be important in the use of many electrosurgical procedures not of the MIS type employing bipolar or unipolar electrodes, for example, for ear, nose and throat surgical procedures.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 5 is a partial perspective view similar to FIG. 1 showing the electrode in its held position corresponding to FIG. 2.

FIGS. 6 and 7 are perspective views of part of the bipolar core assembly of FIG. 1 showing how the electrode contacts are mounted in the core;

DETAILED DESCRIPTION OF THE PREFERRED EMBODIMENTS

One form of bipolar electrode that can be used with the handle of the invention comprises an electrically-insulating tube containing on its interior two electrically-insulated wires which terminate at its remote free working end in balls, hooks or other well-known bipolar shapes that can serve as active electrodes. The opposite end, which is configured to be removably held in the bipolar core assembly, referred to from time-to-time as the head end, is bare but divided into electrically-insulated half round end segments terminating in a recessed section followed by a generally ball-shaped end which is configured to be gripped and held by an electrode holder member which is normally in its closed gripping position but that can be cammed into an open position to release the electrode and that also can be cammed open when the electrode ball end is pushed into the electrode holding member.

Figure 1:
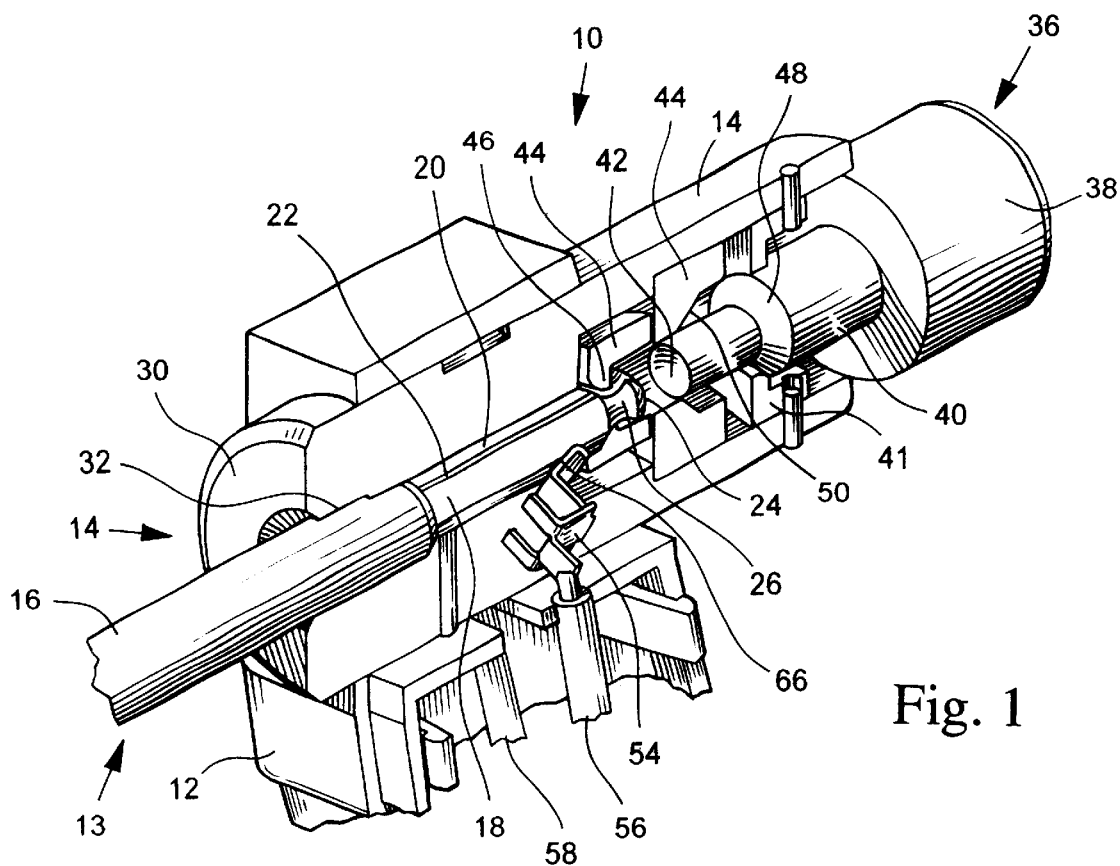
FIG. 1 is a partial perspective view with parts cut-away of one form of handle according to the invention in the process of receiving one form of a bipolar electrode activator for use in an electrosurgical procedure. The electrode working end on the far left has been cut off.

FIG. 1 shows one form of the handle of the invention designated 10. Only one-half of the handle 12 is shown, and part of the core assembly 14 is cut away to show the interior. The electrode 13 with its electrode insulated tube is shown at 16, with the active working end (not shown) at the left. The electrically-insulated divided bare end segments are shown at 18 and 20, divided by an electrically-insulating liner 22. In the preferred form shown in FIG. 1, the bare electrode end terminates in a ball-shaped protuberance 24 separated by an annular recessed section 26 from the bare end. The electrode holder member comprises an outer tubular housing 30 of electrically-insulating material. The latter contains a bore 32 for receiving the head end of the electrode. The bore 32 may be divided into two different-diameter sections containing a shoulder 34 (see FIG. 2) that can act as a stop for the larger diameter insulated end of the electrode.

An activator 36 is provided to eject the electrode. It comprises an external button-shaped member 38, axially aligned with and that extends out of the outer tubular housing 30 and can be operated by the thumb of a user holding the handle 12. The button 38 is connected to a camming member 40 which in turn has a recessed end 42 which contacts or may be slightly spaced from the ball end 24 of the assembled electrode.

The holding function is supplied by an annular member 44, which may be made of a well-known plastic material having memory, having one or more gripping jaws 46 whose normal position is closed with its gripping jaws 46 engaging the recessed section 26 behind the electrode ball end 24. If the gripping jaws 46 are pushed or cammed open, then when the pushing or camming force is released, the plastic material will automatically restore the gripping jaws to its normal closed position. This is accomplished by the material's memory and corresponds to a biasing force tending to close the gripping jaws 46 to its normal closed position.

Figure 1A:
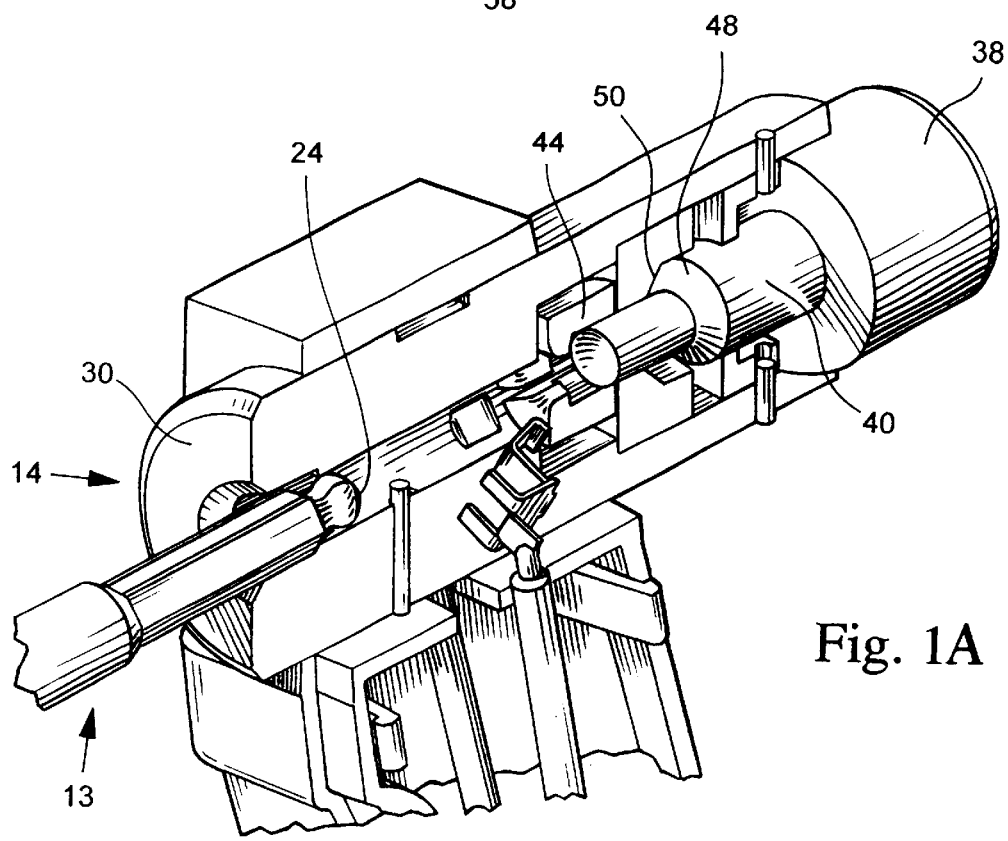
FIG. 1A is a partial perspective view similar to FIG. 1 of the handle of FIG. 1 in the process of removing the bipolar electrode activator.
Figure 2:
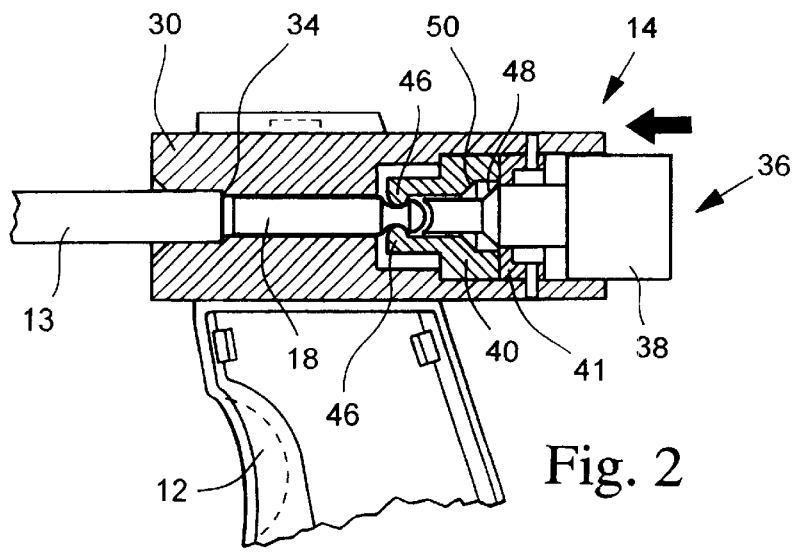
FIGS. 2, 3 and 4 are partial cross-sectional views of the handle and bipolar electrode of FIG. 1 showing how the electrode is held in the handle and how it is ejected for replacement with another electrode.
Figure 3:
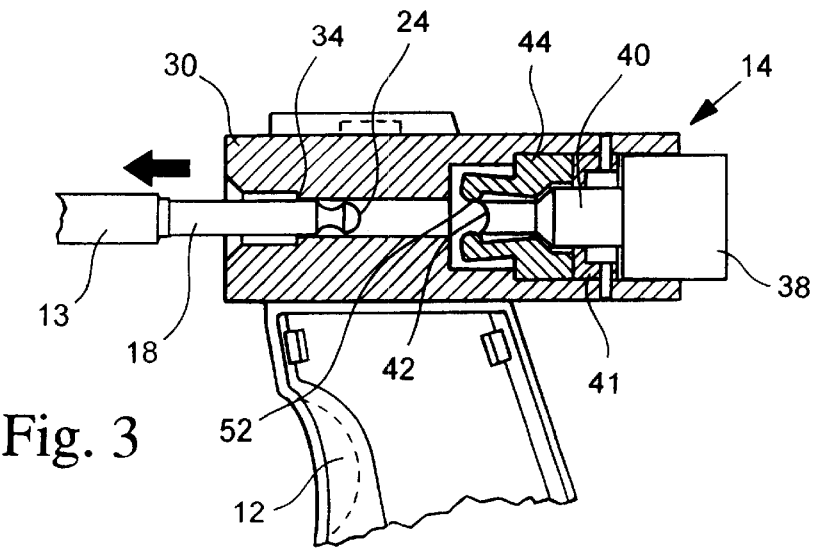
Figure 4:
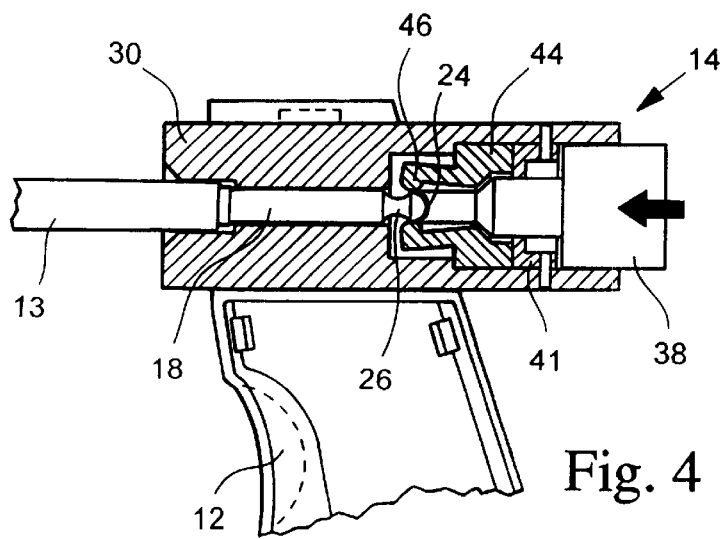

The operation is depicted in FIGS. 2, 3 and 4. FIG. 2 shows the electrode 13 mounted in the core assembly 14. When the user presses the button end 38, the activator 36 is moved to the left in FIGS. 3 and 4, camming open the gripping jaws 46 by a male tapered section 48 on the activator engaging and pushing on a matching female tapered section 50 at the rear of the gripper 44, causing the gripping jaws 46 to open into its open or release position. Then the user can simply withdraw the released electrode 13 from the core assembly, as shown in FIG. 3. To mount the electrode 13, the user pushes the head end into the bore 32, during which process the ball end 24 contacts a beveled entrance 52 to the gripping jaws 46, spreading them apart and allowing the electrode head end to seat in its held position within the gripping jaws 46. The construction is configured so that there is a minimum of wobble or movement of the mounted electrode to enable the surgeon to control accurately the position of the working end during use. A locking member 41 is positioned between the button 38 and the gripper 44. The locking member 41 is fixed as by pins to the outer housing 30 and serves as an internal stop for the ejector 36 (FIG. 3). In FIGS. 1, 1A and 5, while there seems to be two distinct items 44 adjacent the locker 41, in reality they are parts of the same integral gripper 44 as shown in FIG. 3 but which appear separated due to their different elevations in FIGS. 1, 1A and 5

As mentioned, the bare electrode end is divided into two segments 18, 20, each of which is electrically connected to the internal wires leading to the active bipolar electrode working end. Since the electrode can be removed and replaced by another electrode configuration, arrangement must be made to provide appropriate electrical sliding contact within the core to the bare electrical segments 18, 20. This is accomplished in a preferred embodiment by mounting a contact structure 54 for each segment (only the one in front is shown; the other is behind the core and not visible in FIG. 1) in the outer core housing 14, which contact structure 54 is adapted to make a good sliding electrical contact with the adjacent bare electrode segment when the electrode 13 is mounted. FIGS. 1 and 5 show two cables 56, 58 whose ends are connected to a standard 2-prong male connector (not shown) adapted to be plugged into the standard bipolar socket of a conventional electrosurgical apparatus. Each of the cables terminate in one of the two contact structures 54. Each of the contact structures are alike, and comprises a generally U-shaped arrangement of 2 prongs 60 and a common outwardly-facing ear 62 on one side, and a third prong 64 on the opposite side of the U with a laterally-bent ear 66. The two prongs 60 serve to mount the contact structure, as for example with adhesive, in the outer housing 30 with the outwardly-facing ear 62 serving for a hard-wired connection to the cable end, while the laterally-bent ear 66 of the third prong comes into sliding contact with one of the bare end segments 18, 20 when the electrode 13 is mounted. FIGS. 1 and 5 show the laterally-bent ear 66 of the third prong in contact with the front bare segment 18 of the mounted electrode.

A preferred contact mounting arrangement is depicted in FIGS. 6 and 7. The outer core housing 30 is provided with two cut-out sections 68 each with an axially-extending through-slot 70 for receiving the third prong 64 so that the laterally-bent ear 66 is positioned to contact the side 18, 20 of the inserted electrode, and with a transverse blind hole slot 72 for holding the two pronged contact 60 with the outwardly-facing ear 62 accessible for soldering or welding to the cable wire. FIG. 6 shows the mounted position of the contacts 54, and FIG. 7 shows an exploded view of the arrangement. Other contact arrangements will be evident to those skilled in this art.

Figure 8:
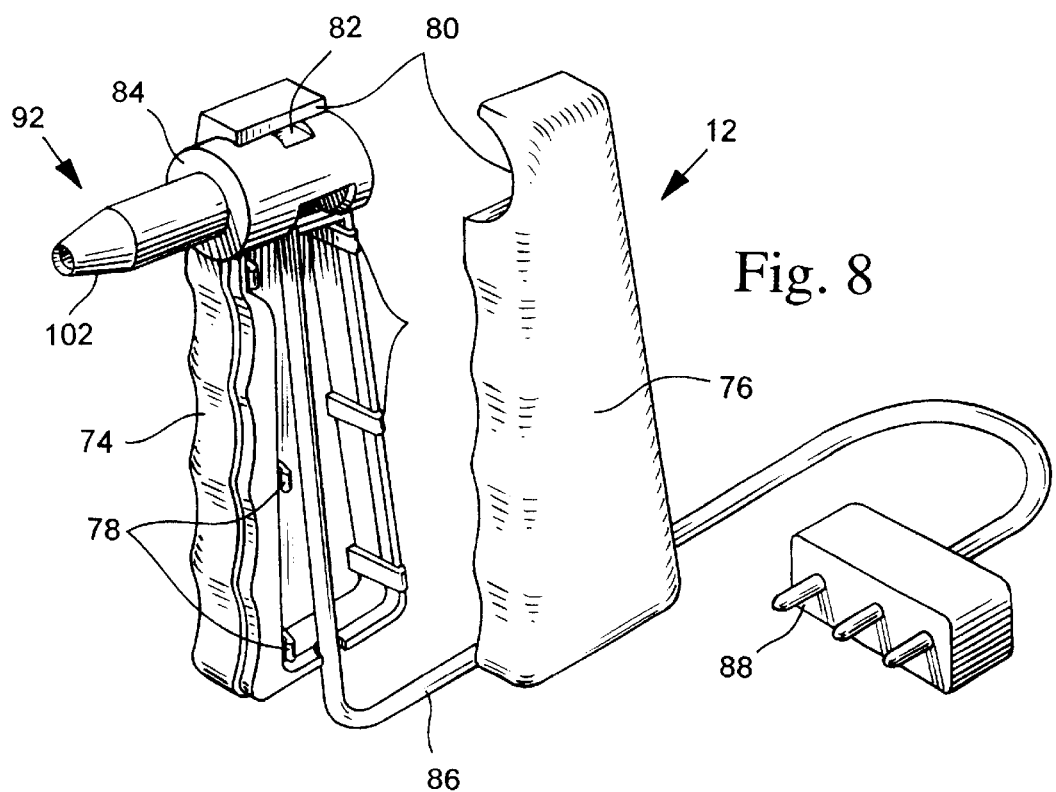
FIGS. 8 and 9 are exploded and assembled perspective views, respectively, of one form of unipolar core assembly in accordance with the invention.

To remove the core assembly 14 and replace with another core assembly (or to assemble together with its attached cables 56, 58 are removed. This is illustrated in FIG. 8. The handle 12 comprises two halves 74, 76 with the left half 74 having six detent members 78 with flanged ends adapted to engage correspondingly shaped slots (not shown) in the right handle half 76. The handle 12, being made of a plastic that has some resilience, allows the user (or assembler) with his hands or with use of a small tool to pry apart the two handle halves 74, 76 which then allows the core assembly 14 to be removed. Each of the handle halves are provided with a concave upper portion 80 configured to fit around and hold a portion of the core outer housing 30 of each of the core assemblies which are similarly configured, for example, as cylinders. The core assemblies may be provided with a positioning slot 82 so that the core occupies the desired position. When the handle halves 74, 76 are snapped together, the core is tightly held within the handle.

Figure 9:
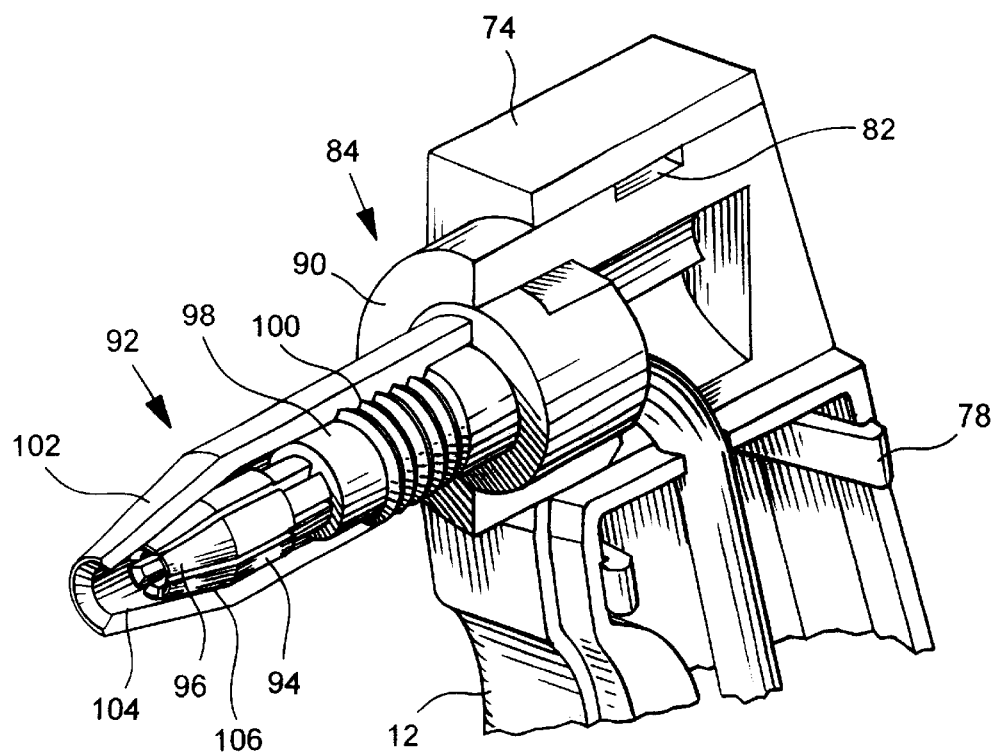

The core assembly 84 in FIGS. 8 and 9 is a unipolar core assembly requiring only a single connection. The cable 86, however, is terminated in a 3 prong male connector 88 for plugging into a corresponding female connector on certain electrosurgical apparatus manufactured by the Ellman Company of Hewlett, N.Y. This is described in U.S. Pat. No. 4,463,759, and no further details are necessary. If desired, the connector 88 can be a more typical banana plug for insertion into the standard unipolar socket on electrosurgical apparatus, or an adapter can be provided for converting the 3 prong connector to a single plug connector. The unipolar core assembly 84 comprises an outer cylindrical housing 90 in which is mounted a conventional collet assembly 92 as described, for example, in U.S. Pat. Nos. 4,657,016 or 5,630,812. The structure comprises an electrically-conductive collet 94, for example, of metal, with slotted jaws 96 mounted in a tubular metal holder 98 provided with external screw threads 100, the whole being surrounded by a nose piece 102 with an internal thread to match the external thread and with a tapered internal surface 104 which engages the tapered outer surface 106 of the collet 94. The collet slotted jaws 96 are sized to accept the standard shank of any one of a number of standard unipolar electrodes (not shown), for example, a loop, ball or needle. When the electrode shank is inserted in the open jaws of the collet 94 and the nose piece 102 rotated clockwise, the nose piece 102 cams the jaws 96 together to clamp the electrode to the collet. When the nose piece 102 is rotated counter clockwise, the electrode shank is released and the electrode can be removed and replaced if desired with another electrode. The unipolar core assembly 84 is held in place within the handle 12 in the same manner as described in connection with the bipolar core assembly 14. The internal cable end (not shown) makes a hard-wired connection to the metallic tube 98 to provide electrosurgical currents to the electrode when the electrosurgical apparatus is activated.

Figure 10:
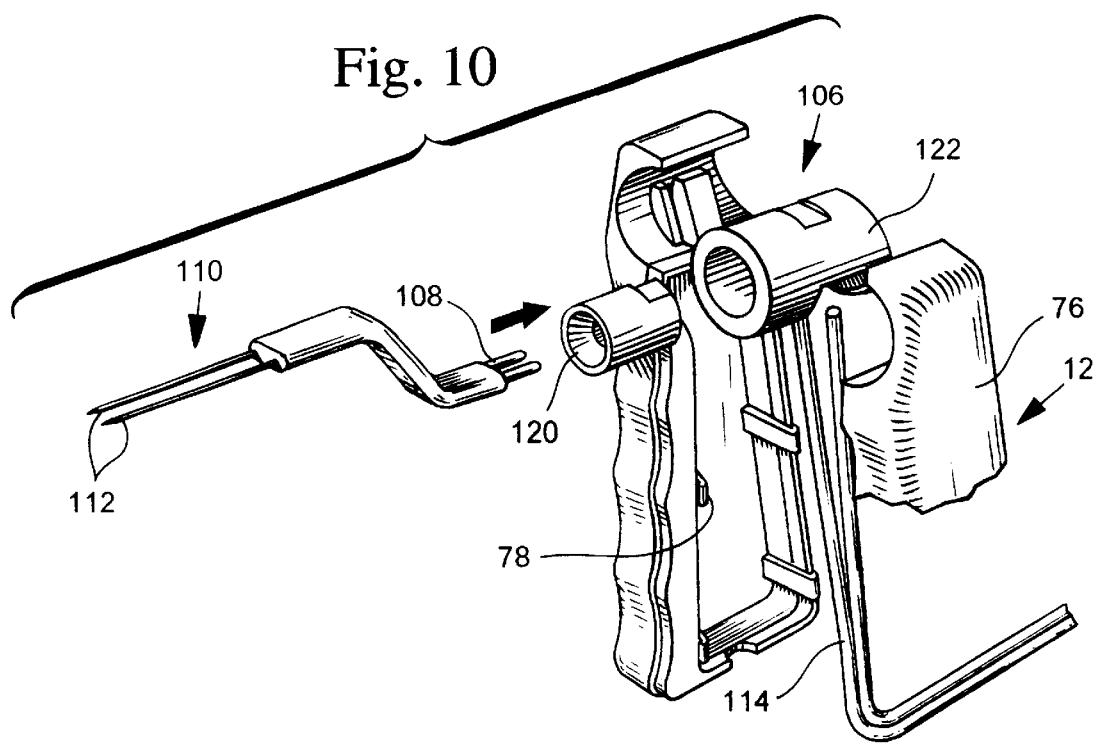
FIGS. 10 and 11 are exploded and assembled perspective views, respectively, of one form of turbinate core assembly in accordance with the invention.
Figure 11:
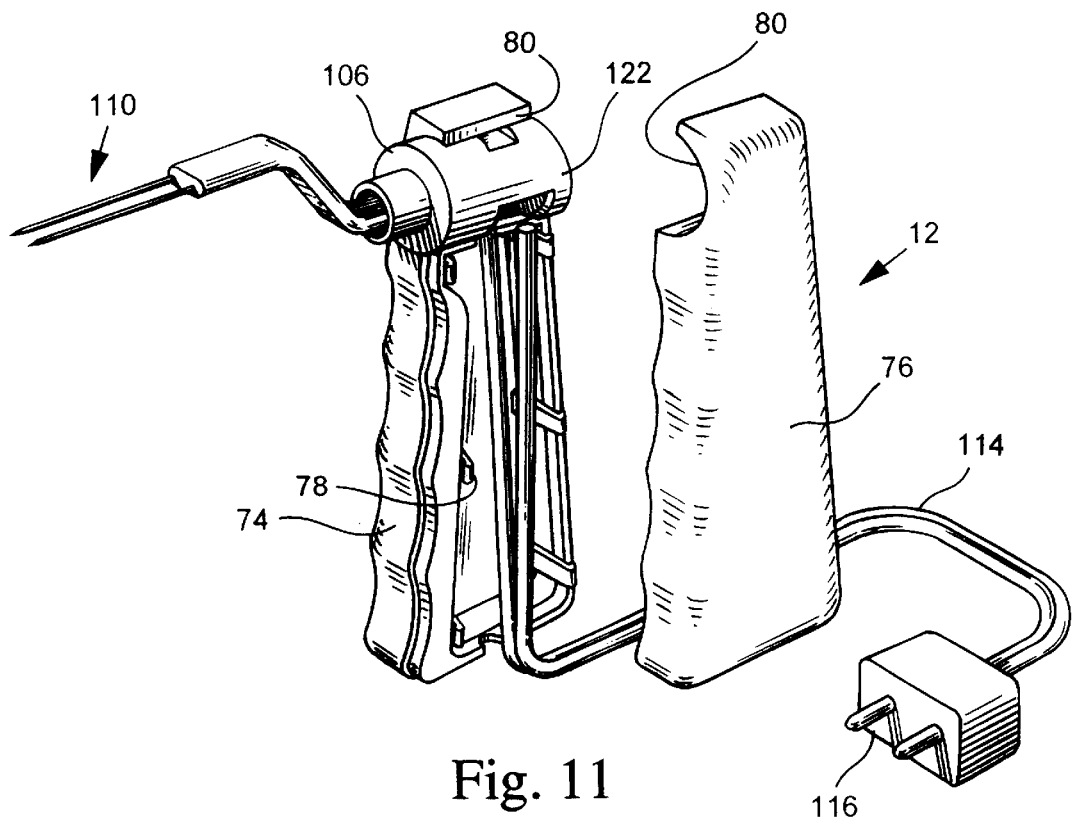

FIGS. 10 and 11 show a third embodiment according to the invention. The handle assembly 12 is the same, but the bipolar core assembly 106 is somewhat different and is configured to receive the bifurcated end 108 of a turbinate electrode 110, which has two active needle ends 112 for insertion in the nostrils of a patient in an ear, nose and throat (ENT) bipolar procedure known as a turbinate procedure. In this case, a cable 114 terminates in a 2-prong male connector 116 for plugging into a corresponding female connector on the electrosurgical apparatus. The two cable ends are hard wired to a 2-hole female electrically-conductive receptacle (not shown) mounted inside an inner electrically-insulating tubular member 120 in turn permanently seated in an outer tubular housing 122, which is mounted in the separable handle 12 in the same manner as the other core assemblies. While the turbinate core assembly 106 is mounted in the handle, the turbinate electrode 110 can be pulled out and, if desired, and replaced by another electrode with a similar bifurcated end 108.

FIG. 5 also shows an elongated electrode 13 with a bent tip 124 of the type described in application Ser. No. 09/393, 286. This kind of electrode is suitable for the MIS procedures described in the application involving a herniated disk, but it will be understood that other bipolar electrode shapes and sizes are equally usable with the versatile electrosurgical electrode handle of the invention.

In summary, the construction of the invention provides a universal handle that is adapted for mounting and unmounting of different core assemblies for carrying out various electrosurgical procedures. The mounting and unmounting is accomplished by constructing the handle in several parts with, preferably, upper concave portions configured to receive and hold core assemblies which are provided with similar outer housing convex portions so that they all can fit within the concave portions of the handle. The handle parts are held together with detent mechanisms which allow them to be easily snapped together and apart as desired. The handle can accommodate a variety of core assemblies that can comprise parts of a family of assemblies capable of both unipolar and bipolar electrosurgical procedures. This feature is usable by the manufacturer who manufactures the entire family but plans to sell each core assembly with its own handle separately. It can also provide a very flexible instrument for the active surgeon who needs or desires the ability to change core assemblies for the same or different procedures.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A family of electrosurgical electrode core assemblies, comprising:

a) a common outer housing having a longitudinal axis and, transverse to the longitudinal axis, a depending handle, b) a plurality of core assemblies, each of said core assemblies comprising an electrode holder having a similarly configured mounting portion for removable mounting within the housing and comprising a bore having a longitudinal axis parallel to that of the outer housing, c) sliding contacts mounted to the electrode holder and having a conductive portion accessible from the electrode holder bore, d) electrical wires connected to the sliding contacts and extending through the depending handle and having a remote end terminating in a connector, e) each of said core assemblies comprising means for removably supporting within its bore an electrosurgical electrode having a conductive portion within the electrode holder when supported, f) each of said electrosurgical electrodes being configured such that when mounted its conductive portion contacts and makes electrical connection with the conductive portion of the sliding contacts, whereby electrosurgical currents are supplied to the electrosurgical electrode when the connector is connected to electrosurgical apparatus.

2. A family of electrosurgical electrode core assemblies as claimed in claim 1, wherein one of the electrode core assemblies is a bipolar core assembly.

3. A family of electrosurgical electrode core assemblies as claimed in claim 2, wherein the bipolar core assembly comprises means for gripping the end of a bipolar electrode and means for ejecting the bipolar electrode from the gripping means.

4. A family of electrosurgical electrode core assemblies as claimed in claim 3, wherein the sliding contacts comprises spaced contacts for making separate electrical contact to two sides of the bipolar electrode.

5. A family of electrosurgical electrode core assemblies as claimed in claim 1, wherein one of the electrode core assemblies is a unipolar core assembly.

6. A family of electrosurgical electrode core assemblies as claimed in claim 5, wherein the unipolar core assembly comprises a collet and nose piece assembly for removably holding an electrode.

7. A family of electrosurgical electrode core assemblies as claimed in claim 1, wherein one of the electrode core assemblies is a turbinate core assembly.

8. A family of electrosurgical electrode core assemblies as claimed in claim 1, wherein the outer housing comprises separable parts configured to receive the electrode holder mounting portion.

9. A family of electrosurgical electrode core assemblies as claimed in claim 8, wherein the separable parts comprise engaging detent structure for snapping together and apart the separable parts.

10. A family of electrosurgical electrode core assemblies as claimed in claim 1, wherein the electrical wires are individually hard wired to the sliding contacts.

11. A family of electrosurgical electrode core assemblies as claimed in claim 1, further comprising means on the core assembly for ejecting an electrode from the core assembly.

12. A family of electrosurgical electrode core assemblies as claimed in claim 1, further comprising means for ejecting an electrode from a core assembly, said ejecting means being aligned with the electrode holder bore.

13. A family of electrosurgical electrode core assemblies as claimed in claim 12, wherein the ejecting means is mounted to the core assembly at an end opposite to the end supporting the electrode.

14. A family of electrosurgical electrode core assemblies as claimed in claim 13, wherein the ejecting means is constructed to apply an axial force to the electrode to eject it.

\* \* \* \* \*